(12) United States Patent
Roy et al.

(10) Patent No.: US 11,298,266 B2
(45) Date of Patent: Apr. 12, 2022

(54) DEPTH FILTER FOR VISUAL PROSTHESES

(71) Applicants: Second Sight Medical Products, Inc., Sylmar, CA (US); Advanced Medical Electronics Corporation, Maple Grove, MN (US); The Johns Hopkins University, Baltimore, MD (US)

(72) Inventors: Arup Roy, Valencia, CA (US); Avraham I. Caspi, Rehovot (IL); Gislin Dagnelie, Baltimore, MD (US); Greg Seifert, St Paul, MN (US); Paul Gibson, Loretto, MN (US)

(73) Assignee: Second Sight Medical Products, Inc., Sylmar, CA (US)

( * ) Notice: Subject to any disclaimer, the term of this patent is extended or adjusted under 35 U.S.C. 154(b) by 48 days.

(21) Appl. No.: 15/835,315

(22) Filed: Dec. 7, 2017

(65) Prior Publication Data
US 2018/0168866 A1   Jun. 21, 2018

Related U.S. Application Data

(60) Provisional application No. 62/431,273, filed on Dec. 7, 2016.

(51) Int. Cl.
| | |
|---|---|
| *A61F 9/08* | (2006.01) |
| *A61N 1/36* | (2006.01) |
| *A61F 9/00* | (2006.01) |
| *G06K 9/00* | (2022.01) |
| *A61F 2/16* | (2006.01) |
| *A61F 9/02* | (2006.01) |

(52) U.S. Cl.
CPC ............ *A61F 9/08* (2013.01); *A61F 9/0017* (2013.01); *A61N 1/36046* (2013.01); *G06K 9/00671* (2013.01); *A61F 2/1624* (2013.01); *A61F 9/022* (2013.01); *A61F 2250/0002* (2013.01)

(58) Field of Classification Search
CPC ...... A61F 9/08; A61F 9/0017; A61N 1/36046
See application file for complete search history.

(56) References Cited

U.S. PATENT DOCUMENTS

| | | |
|---|---|---|
| 4,573,481 A | 12/1986 | Bullara |
| 4,628,933 A | 12/1986 | Michelson |
| 4,837,049 A | 6/1989 | Byers et al. |
| 5,109,844 A | 5/1992 | de Juan, Jr. et al. |
| 5,215,088 A | 6/1993 | Normann et al. |
| 5,935,155 A | 8/1999 | Humayun et al. |
| 6,400,989 B1 | 6/2002 | Eckmiller |
| 6,458,157 B1 | 10/2002 | Suaning |
| 9,811,916 B1 * | 11/2017 | Khokhlov ............ G06T 7/2006 |
| 2009/0312817 A1 * | 12/2009 | Hogle ................. A61B 5/0492 607/54 |
| 2012/0242801 A1 | 9/2012 | Barnes |
| 2013/0253608 A1 | 9/2013 | Zalevsky et al. |

(Continued)

*Primary Examiner* — William J Levicky
(74) *Attorney, Agent, or Firm* — Scott Dunbar (57) ABSTRACT

The present invention is a depth sensing visual prosthesis. By depth sensing objects within an image, items located at a certain depths from the user can be removed to declutter an image. The resulting image presents only objects within a range of depth from the visual prosthesis user. Depth sensing can be accomplished in various ways including structured light, time of flight, or preferably, a stereo camera pair.

9 Claims, 6 Drawing Sheets

(56) References Cited

U.S. PATENT DOCUMENTS

| | | | |
|---|---|---|---|
| 2016/0026253 A1* | 1/2016 | Bradski | G02B 27/0093 |
| | | | 345/8 |
| 2016/0317811 A1* | 11/2016 | Greenberg | A61N 1/36046 |
| 2016/0325096 A1* | 11/2016 | Lui | A61N 1/36046 |
| 2017/0087023 A1* | 3/2017 | Peli | A61N 1/0543 |
| 2018/0177640 A1* | 6/2018 | Quesada | A61F 9/08 |
| 2018/0204329 A1* | 7/2018 | Cutu | G06T 5/50 |

* cited by examiner

| CLASS | TEST | FILTER ON | #TRIALS | S2 %CORRECT | S2 t(MEAN) | S2 t(SD) | S2 t(DIFF) | S3 %CORRECT | S3 t(MEAN) | S3 t(SD) | S3 t(DIFF) |
|---|---|---|---|---|---|---|---|---|---|---|---|
| CHAIR | PRESENT/ABSENT | TRUE | 10 | 100% | 6.2 | 1.2 | -1.7 | 100% | 17.6 | 18.0 | -32.3 |
| CHAIR | PRESENT/ABSENT | FALSE | 10 | 40% | 7.9 | 0.9 | | 80% | 49.9 | 31.7 | |
| CHAIR | LEFT/RIGHT/BOTH | TRUE | 9 | | | | | 89% | 29.6 | 13.2 | 13.6 |
| CHAIR | LEFT/RIGHT/BOTH | FALSE | 9 | | | | | 89% | 16.0 | 7.9 | |
| CHAIR | CLOSER/FARTHER | TRUE | 6 | | | | | 100% | 54.7 | 43.9 | 10 |
| OBJECT | PRESENT/ABSENT | TRUE | 10 | 90% | 12.3 | 3.6 | -12.5 | 100% | 12.3 | 9.6 | -28.4 |
| OBJECT | PRESENT/ABSENT | FALSE | 10 | 50% | 24.8 | 6.5 | | 40% | 40.7 | 24.2 | |
| OBJECT | LEFT/RIGHT/BOTH | TRUE | 9 | | | | | 67% | 33.2 | 22.5 | 20.5 |
| OBJECT | LEFT/RIGHT/BOTH | FALSE | 9 | | | | | 22% | 12.7 | 6.0 | |
| OBJECT | CLOSER/FARTHER | TRUE | 3-7 | | | | | 100% | 75.3 | 83.2 | 2.5 |

| | S4 %CORRECT | S4 t(MEAN) | S4 t(SD) | S4 t(DIFF) | S5 %CORRECT | S5 t(MEAN) | S5 t(SD) | S5 t(DIFF) |
|---|---|---|---|---|---|---|---|---|
| | 100% | 10.5 | 7.5 | -0.1 | 100% | 7.9 | 3.1 | -8.2 |
| | 50% | 10.6 | 7.3 | | 70% | 16.1 | 4.9 | |
| | 56% | 24.3 | 13.7 | 12.1 | | | | |
| | 44% | 12.2 | 8.7 | | | | | |
| | 100% | 139.5 | 38.9 | 20 | | | | |
| | 90% | 8.5 | 6.8 | 0.8 | | | | |
| | 50% | 7.7 | 3.2 | | | | | |
| | 89% | 21.4 | 11.3 | 1.1 | | | | |
| | 56% | 20.3 | 12.7 | | | | | |
| | 88% | 176.7 | 139.0 | 2.5 | | | | |

FIG. 7

DEPTH FILTER FOR VISUAL PROSTHESES

CROSS REFERENCE TO RELATED APPLICATIONS

The present application claims priority to, and incorporates by reference, U.S. Provisional Patent Application 62/431,273, for Depth Filter for a Visual Prosthesis, filed Dec. 7, 2016. The application is also related to, and incorporates by reference, U.S. patent application Ser. No. 14/854,916, for Methods and Systems for Detecting Obstacles for a Visual Prosthesis, filed Sep. 15, 2015, and published as 2016/0317811.

GOVERNMENT RIGHTS NOTICE

This invention was made with government support under EY025136 awarded by the National Institutes of Health. The government has certain rights in the invention.

TECHNICAL FIELD

The present disclosure relates to visual prostheses. More particularly, it relates to depth filtering hardware and software to provide an improved image for a visual prosthesis.

SUMMARY

The present invention is a depth sensing visual prosthesis. By depth sensing objects within an image, items located at a certain depth from the visual prosthesis user can be removed to declutter the image presented to the visual prosthesis user. The resulting image presents only objects within a range of depth from the visual prosthesis user. Depth sensing can be accomplished in various ways including structured light, time of flight, or preferably, a stereo camera pair.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

The overall goal of the present invention is to provide depth-filtered imagery as an input modality to a visual prosthesis. Depth filtering involves the use of a specialized camera, or specialized cameras, and a digital image processing system that detects and removes portions of the viewed scene that represent information outside of a user-preset depth threshold or range of depth. As an example, a walking visual prosthesis user may only wish to see objects between one and eight feet away. This allows the visual prosthesis user to avoid obstacles without distraction from more distant objects. Hence, the system would filter out all image elements not found within the range of depth of one to eight feet.

Applicants have created a prototype system and conducted feasibility testing of the depth filtering system at the Johns Hopkins University (JHU) Lions Vision Center (LVC). We developed a wearable prototype stereoscopic camera system and digital signal processing algorithms to process the imagery and provide a depth map and depth filtering functionality. Following laboratory bench testing and evaluations of this prototype, the stereoscopic camera and image processing system were integrated into an Argus II retinal prosthesis (Second Sight Medical Products) and the complete system was evaluated in an Argus II user at JHU.

We have completed the following:
- Construction of a stereo camera system for real-time depth segmentation of a scene.
- Successful removal of unwanted information from the imagery based on 3D depth map.
- Bench-testing of an image processing algorithm suitable for a body-worn system.
- Observed improved prosthesis utility in human validation testing compared to the unfiltered image provided by the Argus II system.

Applicants have demonstrated that there is an increased success rate, reduced time, and overall reduced burden on the visual prosthesis user as they performed two representative tasks—judging presence, absence, and placement of various pieces of furniture against a cluttered backdrop, and locating and categorizing various objects on a table. The visual prosthesis user who used the prototype system expressed great enthusiasm for the potential of the technology to improve the utility of their implants.

Figure 1:
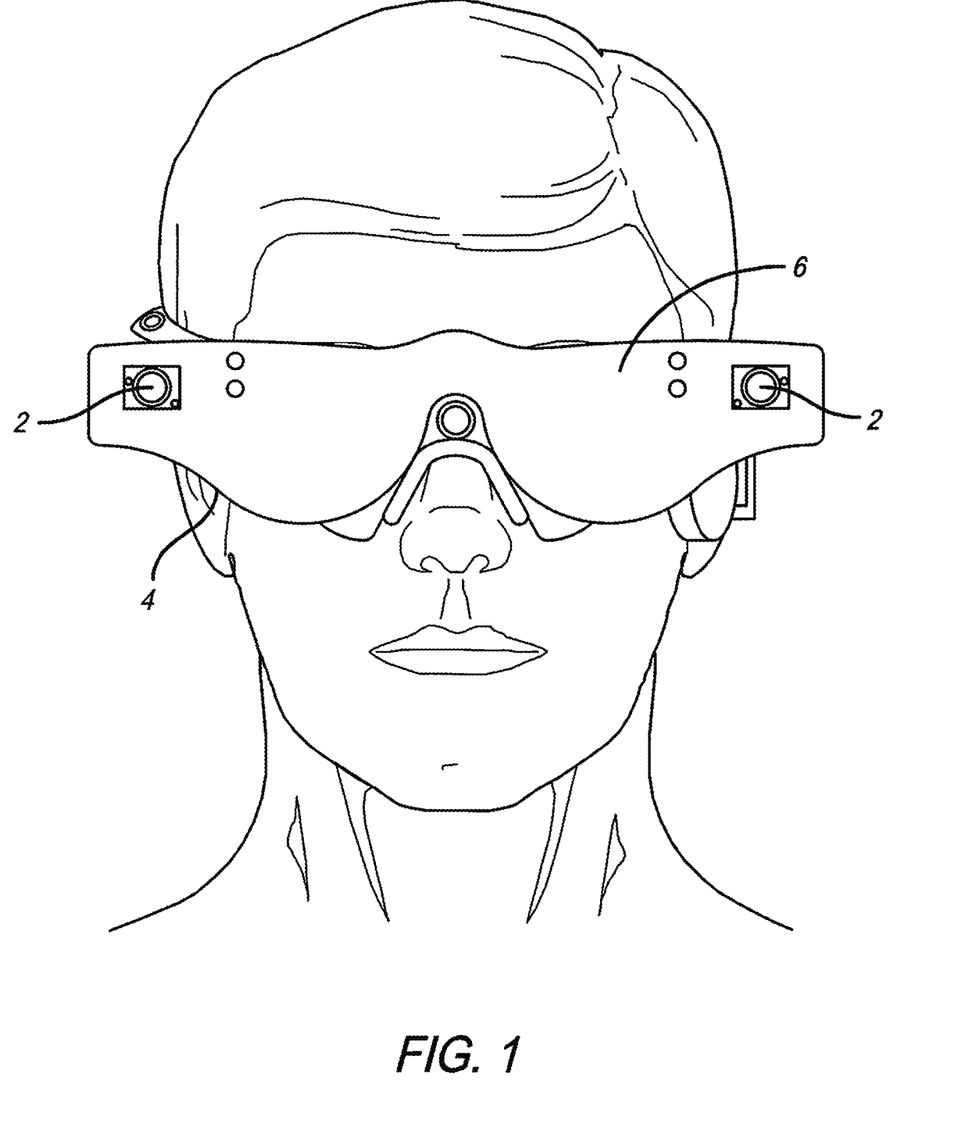
FIG. 1 shows the visual prosthesis glasses of the present invention including a stereo camera pair.

We developed a stereoscopic camera that is mounted to the existing eyewear of the Argus II system FIG. 1. This is a dual-imager camera design with a gate array as the primary data controller and a USB 3.0 interface. Two CMOS cameras 2 mounted on a custom printed circuit board 4 and plastic case 6 were created and the required support firmware and software was written. It should be noted that this application describes a prototype device developed for the purpose of testing the present invention. However, the invention can be incorporated in a device like that described in U.S. patent application Ser. No. 14/854,916, which is described in the Cross Reference to Related Applications.

Figure 3:
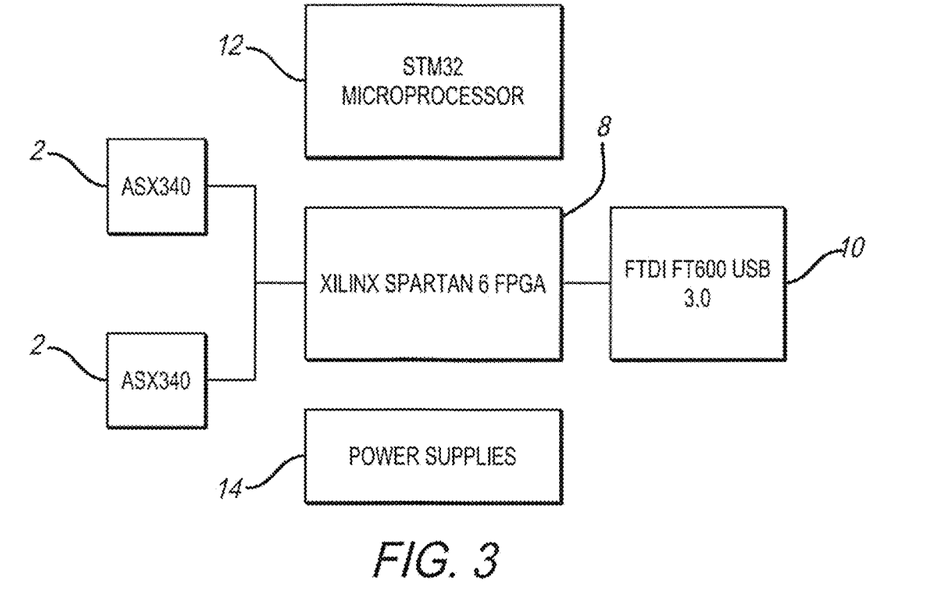
FIG. 3 shows a block diagram of the stereo camera system.

Electronics Hardware Design:

Custom electronics hardware for the prototype USB 3.0 stereo camera system was designed and built. FIG. 3 shows a general block diagram of the hardware components. The main goal of the hardware was to capture and process real-time imagery from two digital CMOS sensors.

We used the ON Semiconductor ASX340AT ¼-inch VGA sensor for the cameras 2 in the system. The two CMOS cameras were interfaced to a Xilinx Spartan field programmable gate array (FPGA) 8. An FPGA is a logic based device well suited for parallel operations in systems requiring fast and large data transfers. The FPGA 8 is responsible for interfacing to each sensor's 2 8-bit parallel port, receiving the data, packetizing, and sending out to the video processing unit (VPU) (see FIG. 5) via USB 3.0 connection 10. While the invention provides for all of the necessary processing to be done in a VPU worn by the patient, for experimental reasons, the processing is described here in a personal computer (PC). It should be clear that the image processing is the same whether carried out in the VPU or by a separate PC.

The USB 3.0 interface 10 was provided by the FTDI Chips FT600 USB 3.0 to FIFO bridge chip. The FT600 supports USB 3.0 Super Speed (5 Gbps). The chip provides a 16-bit parallel interface that is used by the FPGA 8 to quickly and efficiently send imagery data to the internal FIFO memory buffers.

The hardware design contains other required support electronics. A 32-bit STM32 microprocessor from STMicroelectronics is used for overall system control. On boot up the processor 12 performs the following: turns on power to the cameras, loads parameters into each ASX340AT CMOS camera 2 via a serial I2C bus, and notifies the FPGA 8 that the CMOS cameras 2 are now ready to stream real-time video imagery. The system provides several required power supply rails (1.8V, 2.8V, 3.3V) through a combination of low dropout regulator and DC-DC switching power supplies 14. The system power is provided via the USB connection. A miniature inertial sensing system and recording and display software package is used to gather orientation information.

The schematic capture for the hardware design was completed in Altium design studio, which was also used to achieve the custom PCB layout.

Figure 2:
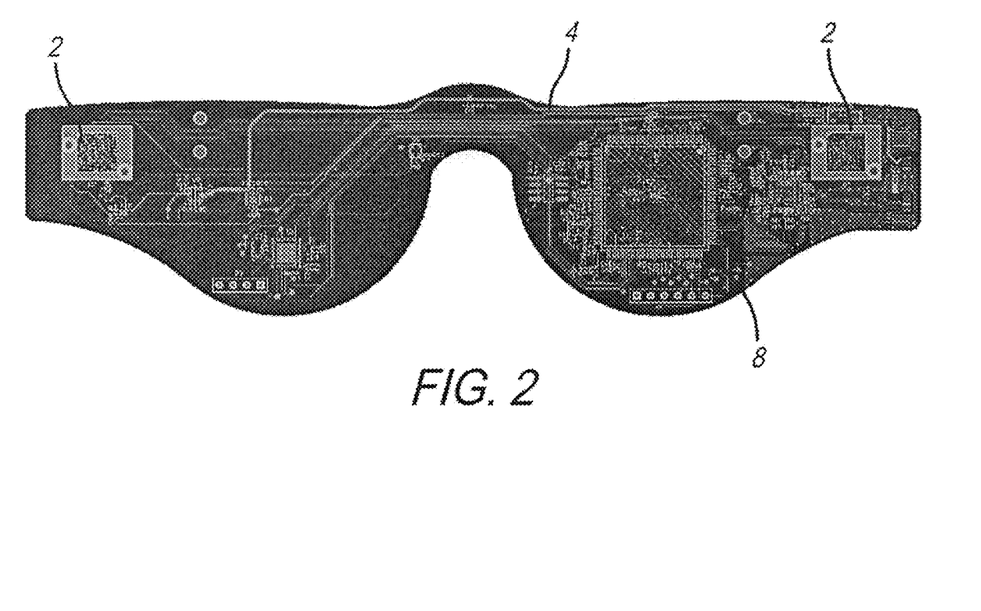
FIG. 2 shows a circuit board layout of the dual camera board.

After the completion of schematic capture and a design review, the printed circuit board (pcb) layout was completed using Altium. A 4-layer 62 mil pcb was selected to provide rigidity to the camera assembly. The pcb also required a controlled dielectric stack-up, since the super speed USB 3.0 differential pair connections had to be carefully designed and routed to ensure signal integrity. FIG. 2 shows an overview of design in the Altium design tool.

The stereo camera 2 pair required the development of firmware for both the Xilinx FPGA 8 and STM32 microprocessor 12. The firmware for the STM32 processor 12 was developed using the C programming language. The firmware captures the register settings for each of the ASX340AT CMOS image cameras 2 required for our system design. On boot, these settings are loaded into the registers of the ASX340AT cameras 2.

The Xilinx FPGA 8 is a logic based device requiring a logic design to be created in a hardware description language. Verilog was chosen for the camera design. The main function of the logic design is to stream the real-time image data from the two CMOS cameras 2 to the VPU for image processing. The logic was broken into two main sections:

ASX340AT Interface—The ASX340AT interface provides a digital interface for capturing each frame's pixel data. An 8-bit parallel data bus is used for sending pixel data. The pixel data is encoded in a YCbCr format meaning for each pixel a 16-bit value is outputted. The interface block captures the incoming pixel data into a 32 Kbyte FIFO buffer. The buffering ensures data is not lost during USB transaction pauses. This block also inserts a frame marker at the beginning of each frame to allow the VPU software to successfully synchronize with the frame data.

USB Interface—The FT600 provides a 16-bit parallel bus to send data to another internal USB memory buffer. The FT600 interface signals the FPGA 8 when data can be sent to the controller. The bus runs at 66 MHz allowing for rapid data transfers.

A package 6 was designed to cover up the electronics for human testing. A thin, light-weight plastic shell was designed and printed. This wraps the electronics in both the front and the back. The package also provides a sturdy clip to allow mounting to the Argus II system glasses. FIG. 1 shows the final packaged stereo camera mounted to the Argus II eye glasses. The system can be implemented in Argus II glasses modified to include two cameras, one mounted on each temple arm, such as shown in US patent application 2016/0317811.

The hardware is capable of processing the 640×480 video at 10 frames per second, with map updates completed within 0.5 s after introduction of a new object in the field. The frame rate is displayed live on the control application in the bottom center section of the user interface screen, when using a PC rather than the VPU. The stereo camera streams a frame rate of 10 frames per second to the PC. The time required for the image processing algorithm was measured and found to support processing at up to 18 frames per second.

The system provides disparity measurement accuracy of: ±4 pixels, i.e. a depth range of [7.5 m, ∞) at 15 m, [3.33 m, 7.5 m] at 5 m, [0.93 m, 1.07 m] at 1 m, [39 cm, 41 cm] at 40 cm. A PC application shows real-time images from both cameras, disparity map, depth segmentation map, and user interface to allow adjustments of the target depth.

Figure 4:
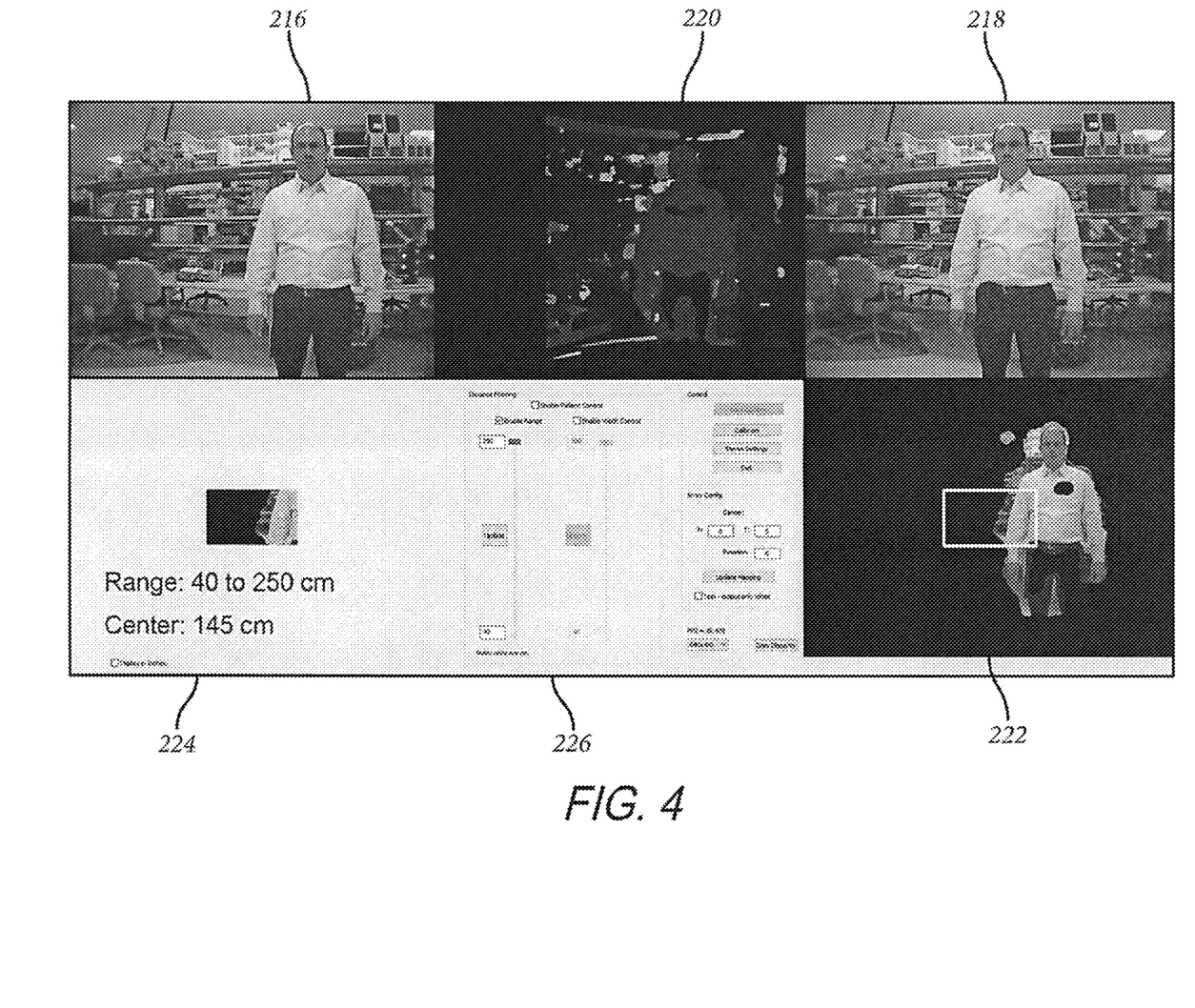
FIG. 4 is a screen from experimental test software demonstrating depth separation.

The PC application was created to provide the image processing component of the depth filtering system and the user interface. A screenshot of the application is shown in FIG. 4. The application was developed using C++ and Microsoft Foundation Class (MFC). The application shows real-time imagery for both left camera 216, right camera 218, disparity image 220, depth filtered image 222, the cropped and rotated image for further processing by the VPU 224, and digital signal processing parameters/settings 226.

The image processing aspects of the application employed the use of the OpenCV image processing library. The library provides support for use of the graphics processing unit (GPU) which was taken advantage of in our application development. OpenCV also provides the camera calibration support required for the generation of the depth information. A separate calibration user interface was created to allow the capture of frames and to perform the calibration. The calibration results are saved for future use and loaded by default when the application is started.

The calibration starts with each camera calibrated individually first. Then a stereo calibration is performed with the individual camera calibrations as part of the input parameters. A rectification map is created from the stereo calibration results to allow undistorting each camera frame to allow for depth information to be found more efficiently.

The front-end of the application handles collecting the incoming frame data from the USB 3.0 driver, synchronizing, and placing the left and right frames into incoming memory buffers for processing. The incoming frame data is converted to gray scale images by extracting intensity information for each pixel.

Figure 5:
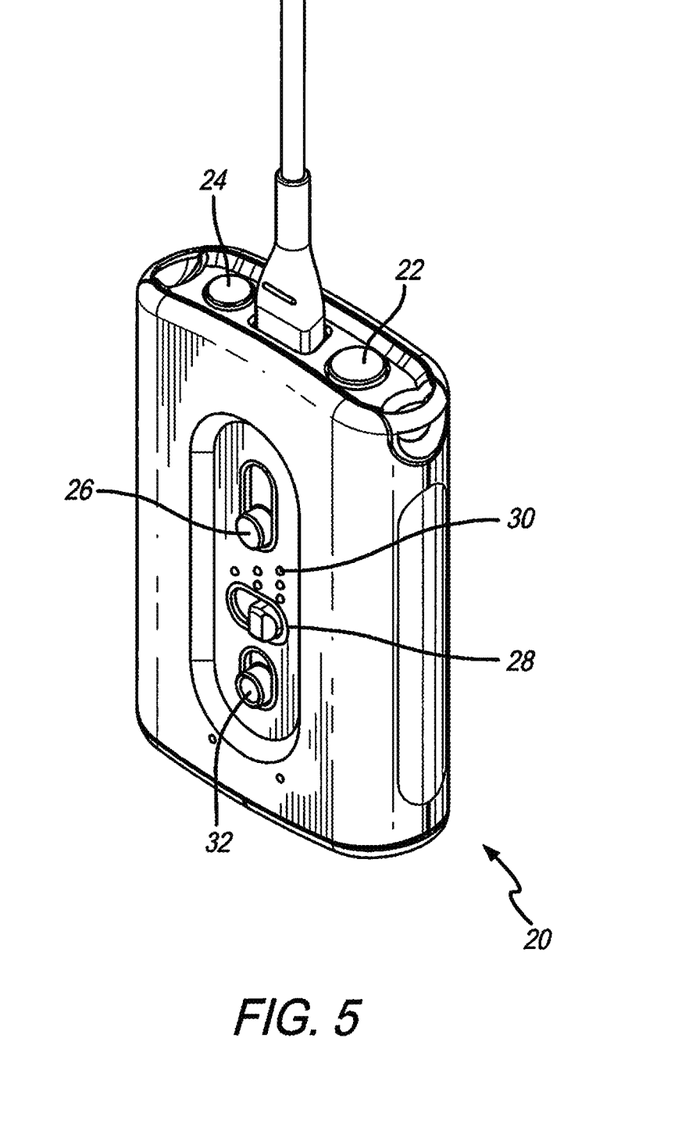
FIG. 5 is the video processing unit of the present invention including slider controls for depth range adjustment.

User control of depth filtering is provided on the VPU. FIG. 5 shows the VPU controls. User input controls on the housing of the video processing unit 2 include a power button 22 and a mute button 24 on the top of the video processing unit 20 housing. The power button is depressed for a predetermined time, about one second, to turn the video processor 20 on or off. The mute button 24 mutes audio feedback. On the face of the video processing unit 20 housing is a slider 26. In the depth sensing mode, the slider 26 controls the depth range of image elements removed by the system. The slider can be programmed for many other functions.

Below the slider 26 is a three position selector switch 28 to choose between programmable options. The three position selector switch includes tactile marks 30 to aid blind users. The three position selector switch 28 is also programmable for function. The position selector switch 28 can select between predefined filters or alter the function of the slider 26 as discussed above. Below the three position selector switch 28 is an invert switch 32. The invert switch 32 inverts the image brightness, light becomes dark and dark becomes light. All of the buttons are programmable to multiple functions. As an example, the power button 22 and the mute button 24 can be programmed as yes and no responses to menu functions. An additional programmable button 14 is on the bottom of the housing.

The depth filtering patient interface is provided via slider control 26 on the VPU. The system supported two depth filtering modes. The first mode allows for objects to be displayed from a near to a far depth range set by slider control 26. The other mode uses the concept of having a bandpass filter with an adjustable width controlled by the selector 28. The bandpass filter center point is then controlled with the slider 26 to allow the user to sweep across the scene finding objects in a particular depth range. We developed a user control interface that can assign the application of the controls in the VPU.

An overview of the image processing algorithm is as follows: 1. Both right and left frame information are rectified using the maps found in the calibration process. This transformation aligns the conjugate epipolar lines so they become collinear and parallel horizontally. 2. Stereo correspondence is then performed to create a disparity map representing the depth information. We use a block matching algorithm to perform the generation of the real-time disparity map. The block matching algorithm is well suited for applications requiring real-time response. 3. The disparity map is filtered further to refine the map before thresholding. 4. Thresholding operations are performed on the map based on the depth filter slider position. A binary image or mask is the output of this operation. 5. The mask is refined further using open and close morphology operations on the mask. 6. This mask is then applied to the left camera image frame to perform the depth filtering to remove objects that are not in the set depth range. After the depth filtering has been applied to the imagery, the image needs to be processed further in preparation for other image processing functions of the VPU. Each patient's implant has a specific orientation and field of view. The application allows for these parameters to be inputted and then performs a crop and rotation on the outgoing imagery to the VPU further image processing.

The depth filtering is demonstrated by controlling the user adjustable depth range on the PC or VPU application. Scenes are staged with objects at known depths to demonstrate accuracy, which are a depth range of [7.5 m, ∞] at 15 m, [3.33 m, 7.5 m] at 5 m, [0.93 m, 1.07 m] at 1 m, [39 cm, 41 cm] at 40 cm.

Map updates within 0.5 s when an object is moved in depth, entering or leaving the selected depth range. Updates are provided at a frame rate of 0.1 s.

The image presented to a visual prosthesis user need not be limited to the luminance in the source image. As an example, a black table may not naturally show up in the limited image provided to a visual prosthesis user. Yet, the black table is very relevant to a visual prosthesis user who is about to walk into it. With depth information available, the system can forward an image to the visual prosthesis user indicating an object within the selected depth range, regardless of the objects natural luminance. This information can be presented with binary contrast, by simply stimulating where an object is detected within the range, and not where no object is detected within the range. This is a symbolic object localization system, since the representation bears little resemblance to the original object.

Figure 6:
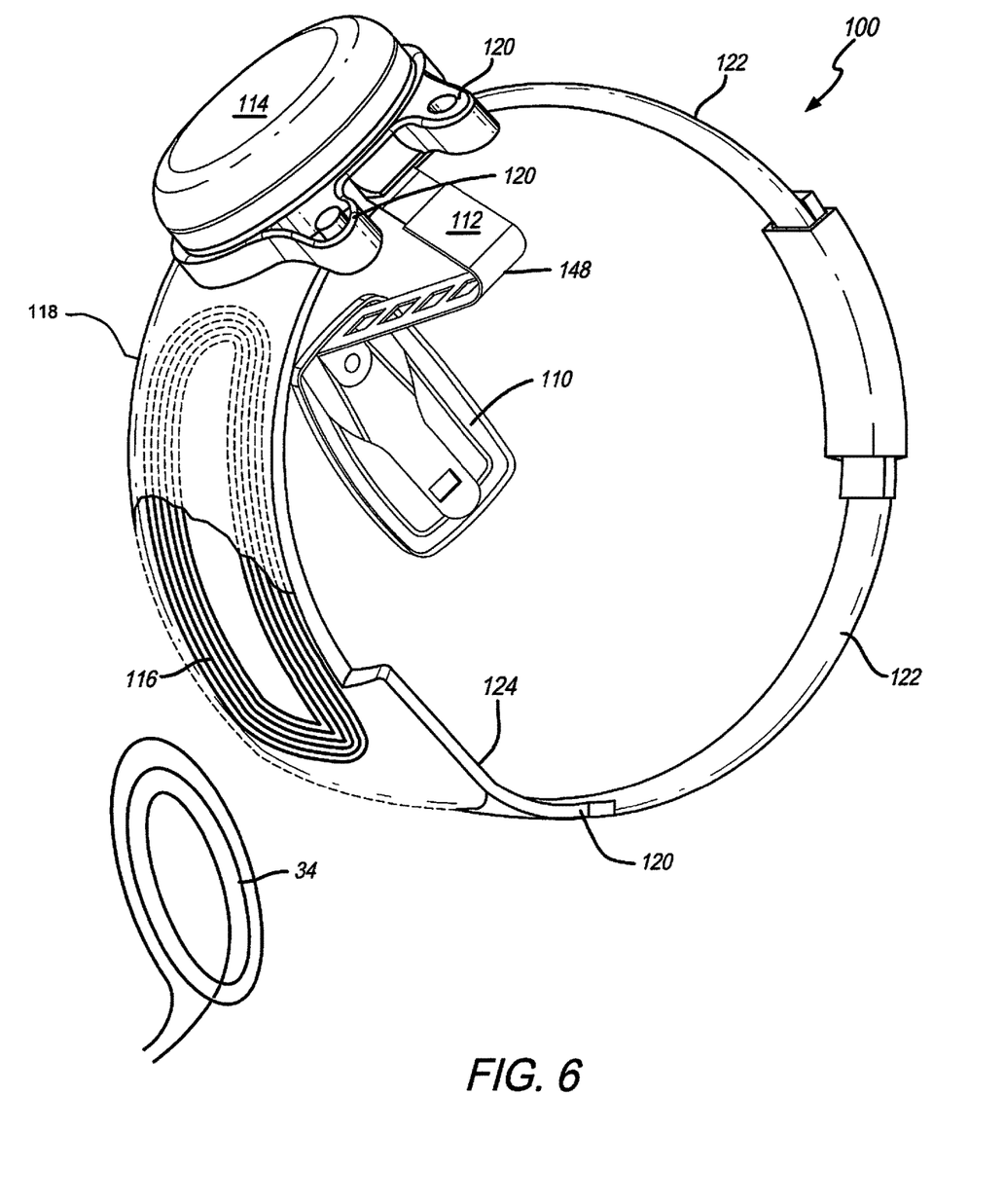
FIG. 6 shows a perspective view of the implanted portion of the visual prosthesis.

FIG. 6 shows a perspective view of the implanted portion 100 of the preferred visual prosthesis. A flexible circuit 112 includes a flexible circuit electrode array 110 which is mounted by a retinal tack (not shown) or similar means to the epiretinal surface. The flexible circuit electrode array 110 is electrically coupled by a flexible circuit cable 112, which pierces the sclera and is electrically coupled to an electronics package 114, external to the sclera.

The electronics package 114 is electrically coupled to a secondary inductive coil 116. Preferably, the secondary inductive coil 116 is made from wound wire. Alternatively, the secondary inductive coil 116 may be made from a flexible circuit polymer sandwich with wire traces deposited between layers of flexible circuit polymer. The secondary inductive coil receives power and data from a primary inductive coil 34, which is external to the body and mounted on the glasses shown in FIG. 1. The electronics package 114 and secondary inductive coil 116 are held together by the molded body 118. The molded body 118 holds the secondary inductive coil 116 and electronics package 114 in the end to end orientation and minimizes the thickness or height above the sclera of the entire device. The molded body 118 may also include suture tabs 120. The molded body 118 narrows to form a strap 122 which surrounds the sclera and holds the molded body 118, secondary inductive coil 116, and electronics package 114 in place. The molded body 118, suture tabs 120, and strap 122 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 116 and molded body 118 are preferably oval shaped. A strap 122 can better support an oval shaped coil. It should be noted that the entire implant is attached to and supported by the sclera. The normal eye moves constantly. The eye moves to scan the scene and also has a jitter motion to improve acuity. Even though such motion is useless in the blind, it typically continues long after a person has lost their sight. By placing the device under the rectus muscles with the electronics package in an area of fatty tissue between the rectus muscles, eye motion does not cause any flexing which might fatigue, and eventually damage, the device.

The molded body 118 narrows into a fin tail 124 at the strap 122. When implanting the visual prosthesis, it is necessary to pass the strap 122 under the eye muscles to surround the sclera. The secondary inductive coil 116 and molded body 118 must also follow the strap 122 under the lateral rectus muscle on the side of the sclera. The implanted portion of the visual prosthesis is very delicate. It is easy to tear the molded body 118 or break wires in the secondary inductive coil 116. In order to allow the molded body 118 to slide smoothly under the lateral rectus muscle, the molded body 118 is shaped in the form of a fan tail 124 on the end opposite the electronics package 114.

We did extensive testing on the system to demonstrate its performance. We mounted the system to a dummy head on a cart to evaluate its performance in laboratory bench testing. The system, while being pushed on a cart, updates the depth map in less than 0.5 s. Updates are provided at a frame rate of 0.1 fps.

The application displays real-time depth-filtered imagery based on user depth setting. This demonstrates the addition and removal of objects based on depth setting while in motion. The application additionally displays inertial reference information as a real-time orientation map. A real-time 3-axis inertial measurement unit and recording/display software are utilized.

IRB approval was obtained and a total of 5 subjects were tested with the developed prototype system. Human testing was conducted on four subjects in a laboratory located at Johns Hopkin University and one subject was tested at a nursing home facility, demonstrating potential use of the prototype outside the laboratory setting.

During testing, the subjects were fitted with the developed prototype and situated in a visually complex environment. Several distant and near activities were arranged in the protocol to challenge the prototype system and evaluate its potential utility to retinal prosthesis recipients. The protocol was expanded to include a wider variety of tasks after the first two subjects achieved positive results.

Figure 7:
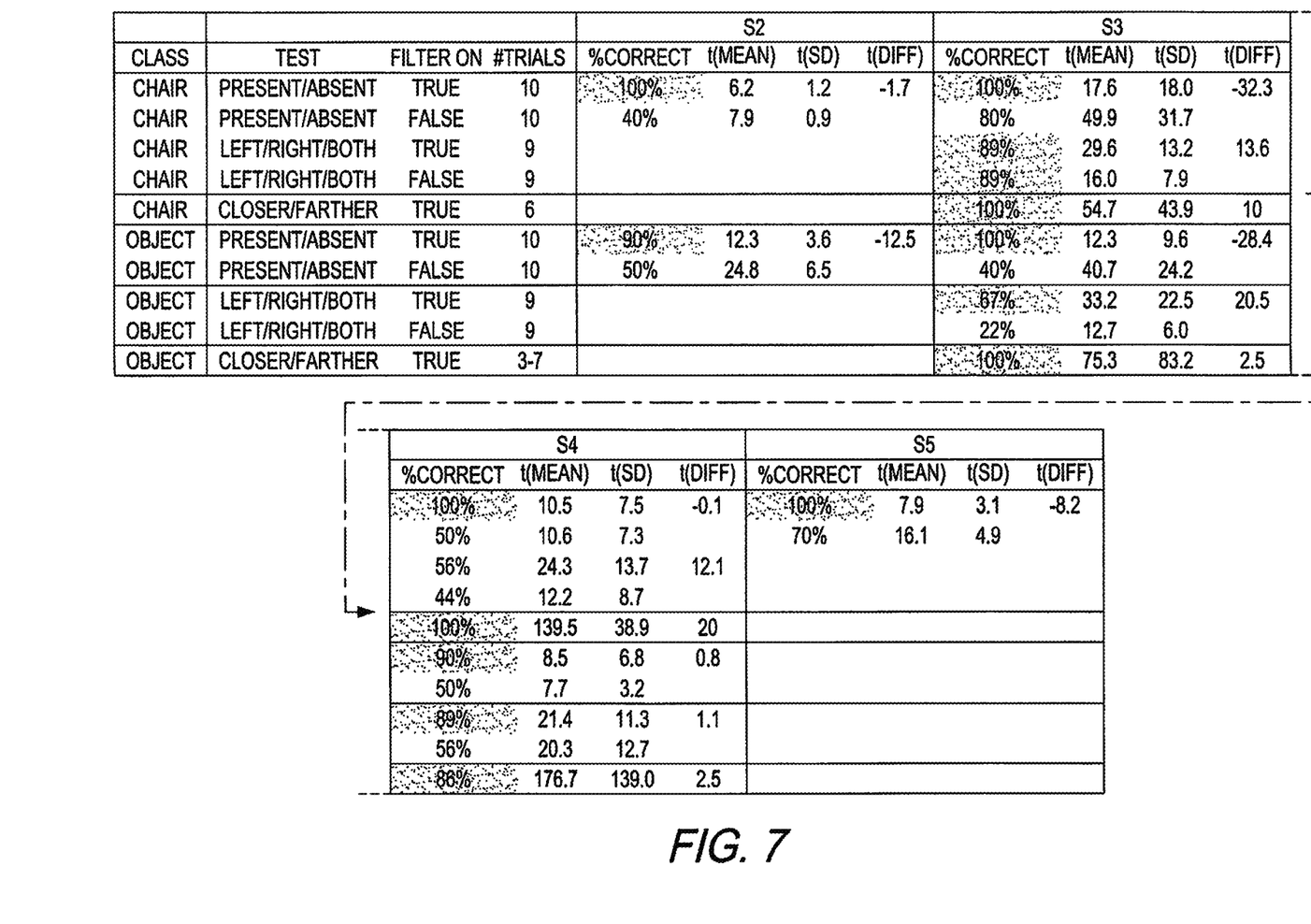
FIG. 7 is a table showing data of four subjects tested with the present invention.

Several observations were made during the evaluations that support the conclusion that depth filtering functionality provides substantial utility to retinal prosthesis users. As a first pilot, one subject was tested at the subject's nursing facility. The system was set-up for the subject's implant and the depth filter maximum depth range was adjusted to different depths during testing. The subject was unable to locate a human target in the room when the depth filtering functionality was disabled. When the depth filtering functionality was enabled, the subject was able to locate a human target. Since this evaluation, and several others carried out with this subject, were part of the protocol development phase, the results are not included in the table in FIG. 7. Other subjects were evaluated for their ability to isolate the location of furniture, for example a chair and standing lamp in the room, with and without the depth filtering functionality. The speed and accuracy of furniture location was significantly improved using the depth filtering technology. Additional tests evaluated the utility of the system to assist users in locating and identifying objects placed on a table in front of the subject. Again, significant performance improvements were observed for patients when utilizing the depth filtering technology. Detailed setup and results information are provided below. Table 1, FIG. 7, summarizes the test results.

Setup 1: Single Chair—

The first test demonstrated depth filtering functionality by allowing a subject to locate a chair placed in a room with background clutter. The following steps were conducted for this test:

1. With depth filtering disabled and without the chair in the scene, the subject was allowed to search the room for any distinct objects for 60 seconds.

2. A chair was added to the scene with the depth filtering still disabled. The subject was allowed to search the scene again for distinct items.

3. Depth filtering was enabled and the above tests were repeated.

4. The chair was added to and taken from scene. The subject was asked if the chair was present or not. This was done 10 times without depth filtering and 10 times with depth filtering; see Table 1, FIG. 7.

Representative Results:

Without filtering or a chair in the room, subject 3 could detect a large white fan in the background, and a chair draped with a flower-pattern tablecloth when added to the scene, at about 2.0 m. When filtering was enabled, the chair was successfully isolated by setting the passband range to 214-280 cm, and the subject could locate the chair easily. As shown in the top rows of Table 1, FIG. 7 all 4 subjects performed error-free and faster with the depth filter; they were not significantly above chance without the filter. With depth filtering disabled and no objects on the table, the subject was allowed to search the table for any distinct objects for 60 seconds.

Setup 2: Two Chairs—

This test is similar to the first set-up with the addition of another chair, for a total of 2 chairs in the scene.

1. Chairs were placed at 2.0 m from the subject, laterally separated by 60 cm.

2. The effect of the chairs fading in and out as the depth filter passband changed was demonstrated to the subject.

3. Subject was asked to describe the chairs present in the scene as Left, Right, or Both. Each scene configuration was presented 3 times in random order for a total of 9 trials; see Table 1, FIG. 7.

This test showed the least effect of the depth filter; primarily because subject 3 could make out the chairs without the filter, once he knew what to look for, whereas subject 4 did detect the chair, but often got confused whether a single chair was standing on the left or on the right.

Setup 3: Two Chairs—

This test used 2 chairs placed at different depths from the subject to allow demonstration of the subject controlling the depth filter's depth setting with slider control.

Chairs were placed 100 and 150 cm away from the subject with a lateral separation of 60 cm.

The experimenter demonstrated how each chair can be isolated by changing filter settings.

The subject was given the slider control and asked to find a setting that would display either the chair on the left or the chair on the right. Subjects performed this task 3-6 times. Times to successfully visualize the target were recorded. Chairs were not moved during this task.

The left chair remained fixed while the right chair depth from the patient was changed randomly. For each depth the subject was asked to find the chairs using the sliding control to adjust depth filter range. The subject reported if the right chair was closer or farther than the left—performed 6 times. Response times were measured; see Table 1, FIG. 7.

This was a fairly difficult task, as can be observed from the longer times required, especially by subject 4; however, discrimination performance was very good.

Setup One: Short Depth Tasks Using Object(s) on a Bare Table.

A table was placed in front of a seated subject with depths on the tabletop ranging from ~20-90 cm. The following objects were used as props for the testing: sugar container, white coffee mug, and 2 M&M bags.

An object was added to the scene with the depth filtering still disabled. The subject was allowed to search the scene again for distinct items.

Depth filtering was enabled and the above tests were repeated.

An object was added into or taken from scene. The subject was asked if the object was present or not. This was done 10 times without depth filtering and 10 times with depth filtering; see Table 1, FIG. 7.

Representative Results:

Without the depth filtering enabled or objects present on the table, subject 3 could perceive the light reflecting off the table. When the tall sugar container was placed on the table the subject was not able to perceive the object itself, only the far edge of the table. When the depth filtering was enabled with a passband of 40-80 cm the subject was able to clearly detect the object on the table. As shown in Table 1, FIG. 7 (data rows 5-6) performance was (near) perfect with the filter on, and at chance with the filter off.

Setup 2: Two Objects—

This test is similar to the first set-up with the addition of another object, total of 2, added to the scene.

Objects were placed at 40 cm from subject, separated laterally by 20 cm.

The effect of the objects fading in and out as the depth filter range changed was demonstrated to the subject.

Subject was asked to describe the objects present in the scene: L/R/Both. Each scene configuration was presented 3 times in random order for a total of 9 trials; see Table 1, FIG. 7.

Contrary to the results with two chairs, subjects showed a distinct benefit from the use of the depth filter. For both subjects tested, performance was not significantly different from chance without the filter, whereas it was above chance with the filter. Subjects were marginally faster without the filter, but this may have been prompted by greater willingness to guess when the filter was not active.

Setup 3: Two Objects—

This test used 2 objects placed at different depths from the subject to allow demonstration of the subject controlling the filter depth setting with slider control.

Objects were placed 30 and 50 cm away from the subject with a lateral separation of 20 cm.

The experimenter demonstrated how each object can be isolated by changing filter settings.

The subject was given the slider control and asked to find a setting that would display either the object on the left or the object on the right. Subjects performed this task 3-6 times. Times to successfully visualize the target were recorded. Objects were not moved during this task.

The left object remained fixed while the right object depth from the patient was changed randomly. For each depth the subject was asked to find the objects using the sliding control to adjust the depth filter range. The subject reported if the right object was closer or farther than the left—performed at least 6 times. Response times were measured; see Table 1, FIG. 7.

Subject 3 Results:

This subject was asked to perform a depth comparison with 2 chairs. After a slow initial trial the subject found the proper adjustment in ~10 s or less. The subject was able to correctly tell if the right chair was closer or farther than the left 5 out of 6 times with a depth range of 250 cm. When the maximum was set to 150 cm, the subject was correct 3 out of 3 times, although this task required much longer than simply finding the chairs.

Using the tall objects on the table, this subject was able to correctly tell which object was closer 6 out of 7 times. In a separate test, the subject was able to correctly tell if the right long and flat object (M&M bag) was closer or farther than the left long and flat object 1 out of 1 times.

Quantitative measures of timing and error scores for the evaluation conditions, without appreciable training, were obtained for at least 2 Argus II wearers on all tasks, and for up to 5 subjects on some tasks.

The results were very positive and the efficacy of the approach thoroughly established. A well-functioning prototype system was designed, built, programmed, and deployed for laboratory evaluation and human subjects testing. What was most encouraging in the human subject tests was the increased success rate, reduced time, and overall reduced burden on the implant wearers as they performed 2 representative tasks—judging presence, absence, and placement of various pieces of furniture against a cluttered backdrop, and locating and categorizing various objects on a table. The visual prosthesis users who used the prototype system expressed great enthusiasm for the potential of the technology to improve the utility of their implants.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A visual prosthesis comprising:
a camera for producing a visual image;
a video processor receiving data from the camera and including a digital image processing system that creates a disparity map, detects and digitally removes portions of the visual image that represent information outside of a preset range of depth from the visual prosthesis user based on the disparity map, and producing stimulation signals based on a portion of the visual image found within the range of depths from the visual prosthesis user;
user controls on the video processor adapted to control depth filtering modes and a band pass filter with adjustable width to control the range of depths visible to the user;
an implantable neurostimulator configured to stimulate visual neural tissue in accordance to the stimulation signals.

2. The visual prosthesis according to claim 1, wherein a second camera with the camera for producing a visual image form stereo cameras and provide depth information to the image processing system.

3. The visual prosthesis according to claim 2, wherein the digital image processing system applies the disparity map to data from the stereo cameras to determine depth information.

4. The visual prosthesis according to claim 3, wherein the disparity map is developed using a block matching algorithm.

5. The visual prosthesis according to claim 1, wherein the camera is configured to be mounted on, and move with, a visual prosthesis user's head.

6. The visual prosthesis according to claim 1, further comprising an inertial sensor to provide orientation information of the camera to the digital image processing system.

7. The visual prosthesis according to claim 1, wherein the digital image processing system removes unwanted image information with a mask.

8. The visual prosthesis according to claim 7, wherein the mask is refined using open and close morphology operations.

9. The visual prosthesis according to claim 1, wherein the stimulation signals are based on the presence or absence of an object within the range of depth, regardless of the luminance level of the object.

* * * * *